US010039862B2

(12) United States Patent
Frankson et al.

(10) Patent No.: US 10,039,862 B2
(45) Date of Patent: Aug. 7, 2018

(54) POLYMER COATING WITH ANTIMICROBIAL MATERIALS AND METHODS FOR PRODUCING (71) Applicant: Cardiac Pacemakers, Inc., St. Paul, MN (US)

(72) Inventors: Danielle Frankson, Dayton, MN (US); Mary M. Byron, Roseville, MN (US); Kurt G. Koubal, Mound, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/205,871

(22) Filed: Jul. 8, 2016

(65) Prior Publication Data

US 2017/0007744 A1    Jan. 12, 2017

Related U.S. Application Data (60) Provisional application No. 62/191,347, filed on Jul. 11, 2015.

(51) Int. Cl.
| *A61L 31/10* | (2006.01) |
| *A61L 31/08* | (2006.01) |
| *A61L 31/16* | (2006.01) |
| *C09D 5/14* | (2006.01) |
| *A01N 59/16* | (2006.01) |
| *A01N 25/10* | (2006.01) |
| *A61L 29/16* | (2006.01) |
| *A61L 29/08* | (2006.01) |

(52) U.S. Cl.
CPC .............. *A61L 31/10* (2013.01); *A01N 25/10* (2013.01); *A01N 59/16* (2013.01); *A61L 29/16* (2013.01); *A61L 31/088* (2013.01); *A61L 31/16* (2013.01); *C09D 5/14* (2013.01); *A61L 29/085* (2013.01); *A61L 2300/102* (2013.01); *A61L 2300/104* (2013.01); *A61L 2300/404* (2013.01); *A61L 2400/12* (2013.01); *A61L 2420/02* (2013.01); *A61L 2420/04* (2013.01); *A61L 2420/06* (2013.01)

(58) Field of Classification Search
CPC ........................ A61L 2300/104; A61L 2420/02
See application file for complete search history.

(56) References Cited

U.S. PATENT DOCUMENTS

| 6,530,951 | B1 | 3/2003 | Bates et al. |
| 7,529,592 | B2 | 5/2009 | Cates et al. |
| 7,947,301 | B2 | 5/2011 | Bischoff et al. |
| 8,282,911 | B2 | 10/2012 | Stark et al. |
| 8,315,700 | B2 | 11/2012 | Citron et al. |
| 8,388,994 | B1 | 3/2013 | Scheer et al. |
| 8,591,531 | B2 | 11/2013 | Buevich et al. |
| 8,927,004 | B1 | 1/2015 | Dehnad et al. |
| 2006/0141015 | A1* | 6/2006 | Tessier .................... A01N 59/16 424/443 |
| 2007/0098806 | A1* | 5/2007 | Ismail ..................... A61K 9/145 424/489 |
| 2008/0051872 | A1 | 2/2008 | Borck |
| 2008/0128315 | A1 | 6/2008 | Buevich et al. |
| 2009/0024097 | A1* | 1/2009 | Okoniewski ........ A61B 17/3498 604/265 |
| 2009/0053278 | A1* | 2/2009 | Fatora .................... A61K 38/08 424/423 |
| 2011/0038131 | A1 | 2/2011 | Hogg et al. |
| 2013/0011456 | A1 | 1/2013 | Kumar et al. |
| 2013/0018448 | A1 | 1/2013 | Folan et al. |
| 2013/0144356 | A1 | 6/2013 | Horn et al. |
| 2013/0177504 | A1* | 7/2013 | Macoviak ................ A61K 8/29 424/10.3 |
| 2014/0220098 | A1 | 8/2014 | Lerner et al. |
| 2015/0086604 | A1 | 3/2015 | Buevich et al. |
| 2016/0367800 | A1 | 12/2016 | Sherwood et al. |

FOREIGN PATENT DOCUMENTS

| DE | 102009007667 A1 | 8/2010 |
| EP | 2099370 A2 | 6/2009 |
| WO | 2008071330 A2 | 6/2008 |
| WO | 2011127478 A1 | 10/2011 |
| WO | 2013191760 A1 | 12/2013 |

OTHER PUBLICATIONS

Grinberg et al., J. Mater. Chem. 8, 2015, 3, 59-64.*
H1465. Implantable Lead Infection Barrier. Jul. 4, 1995. Stokes, et. al. 4 pages.
Hasan, Mahabub, et al. Application of Electrospinning Techniques for the Production of Tissue Engineering Scaffolds: A Review. European Scientific Journal, 10(15): 265-278, May 2014.
Khalil, Abdelrazek Khalil; et al. Preparation and Characterization of Electrospun PLGA/silver Composite Nanofibers for Biomedical Applications. International Journal of Electrochemical Science, 8:3483-3493, 2013.
Kumar, Rakesh. New Technology Offers Alternative Antimicrobial Solution [Online]. Medical Design, Feb. 14, 2014, 6 pages., [retrieved on Apr. 16, 2015]. Retrieved from http://medicaldesign.com/print/materials/new-technology-offers-alternative-antimicrobial-solution.
Wang, Heran, et al. Preparation and Optimization of Silver Nanoparticles Embedded Electrospun Membrane for Implant Associated infections Prevention. American Chemical Society, Applied Materials & Interfaces: 5:11014-11021, 2013.

(Continued)

*Primary Examiner* — Kyle A Purdy
(74) *Attorney, Agent, or Firm* — Faegre Baker Daniels LLP (57) ABSTRACT A method for producing an antimicrobial coating on a surface. The method includes mixing a parylene dimer and an antimicrobial agent to form a mixture, heating the mixture to sublimate the parylene dimer and suspend the antimicrobial agent within the sublimated parylene dimer, pyrolyzing the sublimated parylene dimer to form a parylene monomer while the antimicrobial agent is suspended within the parylene monomer, and condensing the parylene monomer and the antimicrobial agent together on the surface to polymerize the parylene monomer and form a coating containing a parylene polymer and the antimicrobial agent.

10 Claims, 3 Drawing Sheets

(56) References Cited

OTHER PUBLICATIONS

Golda, M et al., Oxygen plasma functionalization of parylene C coating for implants surface: Nanotopography and active sites for drug anchoring, Materials Science and Engineering C, vol. 33, No. 7, Jun. 20, 2013, pp. 4221-4227.

Gorman, William F., A New, General Synthetic Method for the Preparation of Linear Poly-p-xylylenes, Journal of Polymer Science: Part A-1, Jan. 1, 1966, pp. 3027-3039.

International Search Report and Written Opinion issued in PCT/US2016/041572 dated Sep. 29, 2016, 13 pages.

Maggioni et al., An Innovative Pathway towards Nano-Sized Parylene-Based Materials Prepared by Plasma-Based Deposition: Example of Application to the Production of Antimicrobial Materials, Plasma Process. Polym. Mar. 21, 2014, 11, Wiley-VCH Verlag GmbH & Co. KGaA, Weinheim, wileyonlinelibrary.com. pp. 489-495.

International Search Report and Written Opinion issued in PCT/US2016/038032, dated Sep. 9, 2016, 12 pages.

\* cited by examiner

POLYMER COATING WITH ANTIMICROBIAL MATERIALS AND METHODS FOR PRODUCING

CROSS-REFERENCE TO RELATED APPLICATION

This application claims priority to Provisional Application No. 62/191,347, filed Jul. 11, 2015, which is herein incorporated by reference in its entirety.

TECHNICAL FIELD

The present invention relates to preventing infections associated with medical devices. More specifically, the invention relates to coatings and methods for coating medical devices with antimicrobial agents to prevent infections.

BACKGROUND

Medical procedures, and the medical devices employed in the procedures, may expose a patient to a risk of a nosocomial (e.g., hospital-acquired) infection. For example, the average nosocomial infection rate associated with the implantation of pacemakers and implantable cardioverter defibrillators is approximately 3%. In some cases of infection, the implantable medical device, including a device housing and any associated electrical leads or catheters, must be completely removed. Following removal, the infection must be cured and the patient must heal enough to tolerate implantation of a replacement medical device. The costs of such infections are significant, not only intrinsically, but also in terms of the physical and emotional stress suffered by the patient.

Despite infection control practices, such as sterilizing devices, infectious microorganisms may be transmitted from the skin of patients or from a hospital or clinic environment to a medical device. Medical devices in the hospital environment may include for example, catheters, implantable cardio-defibrillators, pacemakers, implantable electrical leads, medical tools, and diagnostic equipment surfaces such as touch pads and displays.

What is needed is a way to prevent nosocomial infections which may result from infectious microorganisms transferred from contaminated medical devices to a patient.

SUMMARY

Example 1 is a method for producing an antimicrobial coating on a surface. The method includes mixing a parylene dimer and an antimicrobial agent to form a mixture, heating the mixture to sublimate the parylene dimer and suspend the antimicrobial agent within the sublimated parylene dimer, pyrolyzing the sublimated parylene dimer to form a parylene monomer while the antimicrobial agent is suspended within the parylene monomer, and condensing the parylene monomer and the antimicrobial agent together on the surface to polymerize the parylene monomer and form a coating containing a parylene polymer and the antimicrobial agent.

In Example 2, the method Example 1, wherein the parylene dimer is selected from the group consisting of [2,2]-paracyclophane, dichloro-[2,2]-paracyclophane, tetrachloro-[2,2]-paracyclophane, and octafluoro-[2,2]-paracyclophane.

In Example 3, the method any of Examples 1-2, wherein the antimicrobial agent is present in the mixture in an amount from about 0.0001 wt. % to about 10 wt. %.

In Example 4, the method any of Examples 1-3, wherein mixing the parylene dimer and the antimicrobial agent includes mixing the parylene dimer and a plurality of antimicrobial nanoparticles, the antimicrobial nanoparticles having an average diameter less than or equal to about 100 nanometers.

In Example 5, the method of Example 4, wherein the antimicrobial nanoparticles have an average diameter greater than or equal to about 20 nanometers and less than or equal to about 60 nanometers.

In Example 6, the method any of Examples 4-5, wherein the antimicrobial nanoparticles include at least one of metallic gold, metallic silver, metallic copper, and combinations thereof.

In Example 7, the method any of Examples 4-6, wherein the antimicrobial nanoparticles include at least one of gold salt, a silver salt, a copper salt, and combinations thereof.

In Example 8, the method of any of Examples 1-7, further including treating the coating with an oxygen-containing plasma.

Example 9 is a device including an antimicrobial coating produced by any of the methods of Examples 1-8, the device including a first surface, a second surface, and an antimicrobial coating covering at least a portion of the first surface and at least a portion of the second surface. The coating includes a parylene polymer distributed throughout the coating, and a plurality of inorganic antimicrobial particles distributed throughout the coating.

In Example 10, the device of Example 9, wherein the second surface is not parallel to the first surface, and wherein a concentration of the inorganic antimicrobial particles in the coating does not differ by more than about 1% between the portion of the first surface and the portion of the second surface.

In Example 11, the device of any of Examples 9-10, wherein the inorganic antimicrobial particles have diameters between about 10 nanometers and about 1 millimeter.

In Example 12, the device of any of Examples 9-11, wherein the inorganic antimicrobial particles include a plurality of inorganic antimicrobial nanoparticles and a plurality of agglomerations of the nanoparticles, wherein the nanoparticles have an average diameter greater than or equal to about 20 nanometers and less than or equal to about 60 nanometers.

In Example 13, the device of any of Examples 9-12, wherein the inorganic nanoparticles have an average diameter of about 40 nanometers.

In Example 14, the device of any of Examples 9-13, wherein the inorganic antimicrobial particles include at least one of metallic gold, metallic silver, metallic copper, and combinations thereof.

In Example 15, the device of any of Examples 9-14, wherein the inorganic antimicrobial particles include at least one of gold salt, a silver salt, a copper salt, and combinations thereof.

Example 16 a method for producing an antimicrobial coating on a surface. The method includes mixing a parylene dimer and an antimicrobial agent to form a mixture, heating the mixture to sublimate the parylene dimer and suspend the antimicrobial agent within the sublimated parylene dimer, pyrolyzing the sublimated parylene dimer to form a parylene monomer while the antimicrobial agent is suspended within the parylene monomer, and condensing the parylene monomer and the antimicrobial agent together on the surface to polymerize the parylene monomer and form a coating containing a parylene polymer and the antimicrobial agent.

In Example 17, the method of Example 16, further including treating the coating with an oxygen-containing plasma.

In Example 18, the method of any of Examples 16-17, wherein the parylene dimer is selected from the group consisting of [2,2]-paracyclophane, dichloro-[2,2]-paracyclophane, tetrachloro-[2,2]-paracyclophane, and octafluoro-[2,2]-paracyclophane.

In Example 19, the method of any of Examples 16-18, wherein the antimicrobial agent is present in the mixture in an amount from about 0.0001 wt. % to about 10 wt. %.

In Example 20, the method any of Examples 16-19, wherein mixing the parylene dimer and the antimicrobial agent includes mixing the parylene dimer and a plurality of antimicrobial nanoparticles, the antimicrobial nanoparticles having an average diameter less than or equal to about 100 nanometers.

In Example 21, the method of Example 20, wherein the antimicrobial nanoparticles have an average diameter greater than or equal to about 20 nanometers and less than or equal to about 60 nanometers.

In Example 22, the method of any of Examples 20-21, wherein the antimicrobial nanoparticles include at least one of metallic gold, metallic silver, metallic copper, and combinations thereof.

In Example 23, the method of Example 22, wherein the antimicrobial nanoparticles consist of metallic silver.

In Example 24, the method of any of Examples 20-21, wherein the antimicrobial nanoparticles include at least one of gold salt, a silver salt, a copper salt, and combinations thereof.

In Example 25, the method of Example 24, wherein the antimicrobial nanoparticles are selected from a group consisting of silver nitrate, silver chloride, and combinations thereof.

Example 26 is a device including an antimicrobial coating. The device includes a first surface, a second surface that is not parallel to the first surface, and an antimicrobial coating covering at least a portion of the first surface and at least a portion of the second surface. The coating includes a parylene polymer distributed throughout the coating, and a plurality of inorganic antimicrobial particles distributed throughout the coating. A concentration of the inorganic antimicrobial particles in the coating does not differ by more than about 1% between the portion of the first surface and the portion of the second surface.

In Example 27, the device of Example 26, wherein the parylene polymer is selected from the group consisting of poly(p-xylylene), poly(monochloro-p-xylylene), poly(dichloro-p-xylylene), and poly(tetrafluoro-p-xylylene).

In Example 28, the device of Example 27, wherein the parylene polymer is poly(monochloro-p-xylylene).

In Example 29, the device of any of Examples 26-28, wherein the inorganic antimicrobial particles have diameters between about 10 nanometers and about 1 millimeter.

In Example 30, the device of any of Examples 26-29, wherein the inorganic antimicrobial particles include a plurality of inorganic antimicrobial nanoparticles and a plurality of agglomerations of the nanoparticles, wherein the nanoparticles have an average diameter greater than or equal to about 20 nanometers and less than or equal to about 60 nanometers.

In Example 31, the device of Example 30, wherein the inorganic nanoparticles have an average diameter of about 40 nanometers.

In Example 32, the device of any of Examples 26-31, wherein the inorganic antimicrobial particles include at least one of metallic gold, metallic silver, metallic copper, and combinations thereof.

In Example 33, the device of Example 32, wherein the inorganic antimicrobial particles include metallic silver.

In Example 34, the device of any of Examples 26-33, wherein the inorganic antimicrobial particles include at least one of gold salt, a silver salt, a copper salt, and combinations thereof.

In Example 35, the device of Example 34, wherein the inorganic antimicrobial particles are selected from a group consisting of silver nitrate, silver chloride, and combinations thereof.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 2A, 2B, and 2C are views of a device including a surface having an antimicrobial coating in accordance with embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
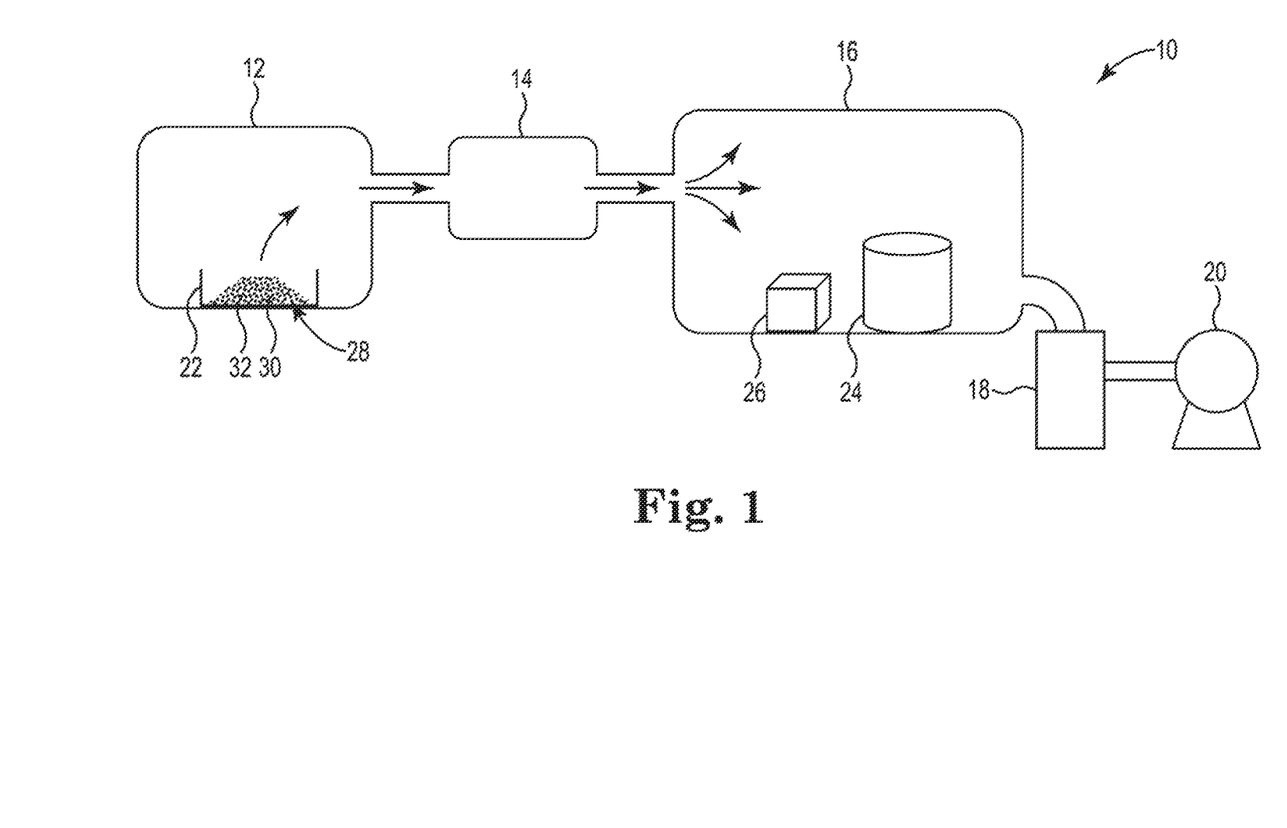
FIG. 1 is a schematic view of a system for producing an antimicrobial coating on surfaces of devices in accordance with embodiments of the present invention.

FIG. 1 is a schematic view of a system for producing an antimicrobial coating on surfaces of devices in accordance with embodiments of the present invention. FIG. 1 shows a deposition system 10 may include a vaporizer 12, a furnace 14, a deposition chamber 16, a cold trap 18, and a pump 20. The vaporizer 12 may include a removable boat 22. The vaporizer 12 may be a vacuum chamber which may be heated and maintained at a desired temperature. The furnace 14 may be another vacuum chamber which may also be heated and maintained at a desired temperature different from the temperature of the vaporizer 12. The deposition chamber 16 is yet another vacuum chamber. The cold trap 18 may be a device employing cooling to condense materials within. The cold trap 18 may be cooled by refrigeration or by a cryogenic gas, such as liquid nitrogen. The pump 20 may be a mechanical vacuum pump, for example, a rotary vane vacuum pump. As shown in FIG. 1, the vaporizer 12, the furnace 14, and the deposition chamber 16 may all be fluidly connected. The vacuum pump 20 may be fluidly connected to the deposition chamber 16 through the cold trap 18. The deposition system 10 may be a commercially available system, such as a Specialty Coating Systems™ PDS 2035CR Parylene Deposition System from Specialty Coating Systems, Inc. of Indianapolis, Ind.; or a Para Tech™ Model 4000V Parylene Coating System from Para Tech Coating, Inc. of Aliso Viejo, Calif.

Also shown in FIG. 1 are exemplary devices 24, 26 having surfaces to be coated with an antimicrobial coating. In some embodiments, the devices 24, 26 each have at least a first surface and a second surface in which the second surface is not parallel to the first surface as described below in reference to FIGS. 2A-2C for device 24. While device 24 is illustrated as a cylinder and device 26 is illustrated as a cube, it is understood that embodiments include other shapes, for example, pyramids, spheres, ovoids, ellipsoids, and other three-dimensional shapes or combinations of three-dimensional shapes including surfaces that are not parallel to each other. The devices 24, 26 may be, for example, catheters, implantable cardio-defibrillators, pacemakers, implantable electrical leads, medical tools, and diagnostic equipment surfaces, including touch pads and displays, or any combination of these devices. In some embodiments, devices 24, 26 may be a device for use in a hospital operating room.

Also shown in FIG. 1 is a mixture 28 including a parylene dimer 30 and an antimicrobial agent 32. The mixture 28 may be formed by mixing the parylene dimer 30 and the antimicrobial agent 32. In some embodiments, the antimicrobial agent 32 may be present in the mixture 28 in an amount as little as about 0.0001 weight percent (wt. %), about 0.0005 wt. %, about 0.001 wt. %, about 0.005 wt. %, or about 0.01 wt. %, or as great as about 0.1 wt. %, about 0.5 wt. %, about 1 wt. %, about 5 wt. %, or about 10 wt. %, or may be present within any range defined between any pair of the foregoing values. In exemplary embodiments, the antimicrobial agent 32 may be present in the mixture 28 in an amount from about 0.0001 wt. % to about 10 wt. %, from about 0.0005 wt. % to about 5 wt. %, from about 0.001 wt. % to about 1 wt. %, from about 0.005 wt. % to about 0.5 wt. %, or from about 0.01 wt. % to about 0.1 wt. %. In some exemplary embodiments, the antimicrobial agent 32 may be present in the mixture 28 in an amount of about 0.05 wt. %.

In some embodiments, the parylene dimer 30 may be [2,2]-paracyclophane according to Formula I below, also referred to as parylene N dimer. In other embodiments, the parylene dimer 30 may be dichloro-[2,2]-paracyclophane according to Formula II below, also referred to as parylene C dimer. In some embodiments, the parylene dimer 30 may be tetrachloro-[2,2]-paracyclophane according to Formula III, also known as parylene D dimer. In some embodiments, the parylene dimer 30 may be octafluoro-[2,2]-paracyclophane according to Formula IV, also known as parylene AF-4 dimer. The parylene dimer 30 may be available in the form of a solid, such as a powder.

Formula I

Formula II

Formula III

Formula IV

In some embodiments, the antimicrobial agent 32 may be a plurality of antimicrobial particles having an average diameter less than about 1 millimeter. In other embodiments, the antimicrobial particles may have an average diameter less than about 0.5 millimeters, less than about 0.2 millimeters, less than about 0.05 millimeters, less than about 0.02 millimeters, less than about 0.01 millimeters, less than about 5,000 nanometers, less than about 2,000 nanometers, less than about 1,000 nanometer, or less than about 500 nanometers.

In some embodiments, the plurality of antimicrobial particles may include a plurality of antimicrobial nanoparticles having an average diameter less than or equal to about 100 nanometers. In some embodiments, the nanoparticles may have an average diameter as little as about 5 nanometers, 10 nanometers, about 20 nanometers, or about 30 nanometers, or as great as about 50 nanometers, about 60 nanometers, about 70 nanometers, or about 100 nanometers, or may have an average diameter within any range defined between any pair of the foregoing values. In exemplary embodiments, the nanoparticles may have an average diameter from 5 to 100 nanometers, 10 to 70 nanometers, from 20 to 60 nanometers, or from 30 to 50 nanometers. In some embodiments, the nanoparticles may have an average diameter of about 40 nanometers.

In some embodiments, the antimicrobial particles may be inorganic antimicrobial particles. In some embodiments the inorganic antimicrobial particles may include at least one of metallic silver, metallic gold, metallic copper, and combinations thereof. Metallic silver, metallic gold, and metallic copper mean silver, gold, and copper in the form of metal ions metallically bonded to other metal ions. In some embodiments, the inorganic antimicrobial particles may include metallic silver. Alternatively or additionally, in some embodiments the inorganic antimicrobial particles may include at least one of a silver salt, a gold salt, a copper salt and combinations thereof. A silver salt, a gold salt, and a copper salt mean silver, gold, and copper in the form of metal ions ionically bonded to non-metal ions (e.g. chloride, nitrate). In some embodiments, the inorganic antimicrobial particles may include a silver salt, for example, silver nitrate, silver chloride, and combinations thereof. In some embodiments, the inorganic antimicrobial particles may be antimicrobial nanoparticles as described above.

In operation, the devices 24, 26 may be placed within the deposition chamber 16 as shown in FIG. 1. The mixture 28 may be placed within the removable boat 22, and the removable boat 22 placed within the vaporizer 12. Air may be removed from the vaporizer 12, the furnace 14, and the deposition chamber 16 through the cold trap 18 by one or more vacuum pumps, such as vacuum pump 20. The furnace 14 may then be heated to a temperature sufficient to pyrolize the parylene dimer 30. The temperature sufficient to pyrolize the parylene dimer 30 may depend on which type of parylene dimer is employed. For example, if the parylene dimer 30 is parylene C, the pyrolization temperature may be between about 680° C. and about 685° C. In other embodiments, the pyrolization temperature may be as low as about 550° C., about 615° C., or about 680° C., or as high as about 690° C., about 695° C., or about 700° C., or within any range defined between any pair of the foregoing values. In exemplary embodiments, the pyrolization temperature may be from about 550° C. to about 700° C., from about 615° C. to about 695° C., or from about 680° C. to about 690° C. In some exemplary embodiments, the pyrolization temperature may be about 685° C. In some embodiments, the pyrolization temperature may increase as the absolute pressure in the furnace 14 increases.

As the furnace 14 approaches the pyrolization temperature and the deposition system 10 has reached a base pressure, the vaporizer 12 may be heated to a temperature sufficient to sublimate or vaporize the parylene dimer 30. In some embodiments, the vaporization temperature may be as low as about 110° C., about 130° C., or about 145° C., or as high as about 155° C., about 160° C., or about 170°, or within any range defined between any pair of the foregoing values. In exemplary embodiments, the vaporization temperature may be from about 110° C. to about 170° C., from about 130° C. to about 160° C., or from about 145° C. to about 155° C. In some exemplary embodiments, the vaporization temperature may be about 150° C.

As the parylene dimer 30 sublimates, the antimicrobial agent 32 may be carried along or suspended within the vaporized parylene dimer 30. In some embodiments, the sublimation of the parylene dimer 30 may increase the pressure within the vaporizer 12 relative to the pressure in the furnace 14, and drive a flow of the vaporized parylene dimer 30 and the suspended antimicrobial agent 32 into the furnace 14.

Within the furnace 14, the parylene dimer 30 may pyrolize, or cleave, into a parylene monomer. The antimicrobial agent 32 remains suspended and is carried along with the parylene monomer. In some embodiments, the parylene monomer may be according to Formula V below if the parylene dimer 30 is parylene N dimer. In other embodiments, the parylene monomer may be according to Formula VI below if the parylene dimer 30 is parylene C dimer. In some embodiments, the parylene monomer may be according to Formula VII below if the parylene dimer 30 is parylene D dimer. In some embodiments, the parylene monomer may be according to Formula VIII below if the parylene dimer 30 is parylene AF-4 dimer.

Formula V

Formula VI

Formula VII

Formula VIII

The parylene monomer and the suspended antimicrobial agent 32 flow from the furnace 14 into the deposition chamber 16 where the parylene monomer and the antimicrobial agent 32 condense onto surfaces at about room temperature (e.g. about 25° C.). The devices 24, 26 may be at about room temperature, so the parylene monomer and the antimicrobial agent condense onto all exposed surfaces of the devices 24, 26. Once condensed onto a surface, the parylene monomer polymerizes to form an antimicrobial coating 34 including a parylene polymer 36 and the antimicrobial agent 32 as described below in reference to FIG. 2.

In some embodiments, the parylene polymer 36 may be poly(p-xylylene) according to Formula IX below, also referred to as parylene N, if the parylene dimer 30 is parylene N dimer. In other embodiments, the parylene polymer 36 may be poly(monochloro-p-xylylene) according to Formula X below, also referred to as parylene C, if the parylene dimer 30 is parylene C dimer. In some embodiments, the parylene polymer 36 may be poly(dichloro-p-xylylene) according to Formula XI below, also referred to as parylene D, if the parylene dimer 30 is parylene D dimer. In some embodiments, the parylene polymer 36 may be poly(tetrafluoro-p-xylylene) according to Formula XII below, also referred to as parylene AF-4, if the parylene dimer 30 is parylene AF-4 dimer.

Formula IX

Formula X

Formula XI

Formula XII

The pump 20 pumps away reaction products and any air that may leak into the deposition system 10 to maintain a pressure gradient across the deposition system 10. In some embodiments, the absolute pressure within the vaporizer 12 may be as low as about 13 Pa (0.1 Torr), or about 40 Pa (0.3 Torr), or as high as about 107 Pa (0.8 Torr), or about 133 Pa (1 Torr), or within any range defined between any pair of the foregoing values. In exemplary embodiments, the absolute pressure within the vaporizer 12 may be from about 13 Pa (0.1 Torr) to about 133 Pa (1 Torr), or from about 40 Pa (0.3 Torr) to about 107 Pa (0.8 Torr). In exemplary embodiments, the absolute pressure within the vaporizer 12 may be about 67 Pa (0.5 Torr). In some embodiments, the absolute pressure within the deposition chamber 16 may be as low as about 1.3 Pa (0.01 Torr), about 2.7 Pa (0.02 Torr), or about 6.7 Pa (0.05 Torr), or as high as about 13 Pa (0.1 Torr), about 27 Pa (0.2 Torr), or about 67 Pa (0.5 Torr), or within any range defined between any pair of the foregoing values. In exemplary embodiments, the absolute pressure within the deposition chamber 16 may be from about 1.3 Pa (0.01 Torr) to about 67 Pa (0.5 Torr), from about 2.7 Pa (0.02 Torr) to about 27 Pa (0.2 Torr), or from about 6.7 Pa (0.05 Torr) to about 13 Pa (0.1 Torr). In exemplary embodiments, the absolute pressure within the deposition chamber 16 may be about 9.3 Pa (0.07 Torr). The pressure within the deposition chamber 16 may increase as the parylene monomer and the suspended antimicrobial agent 32 flow from the furnace 14 into the deposition chamber 16. The absolute pressure in the deposition chamber 16 may be lower than the absolute pressure within the vaporizer 12. The cold trap 18 may condense any reaction products (e.g. parylene monomer) escaping from the deposition chamber 16 to protect the pump 20.

Portions of the devices 24, 26 may be masked (not shown) such that parylene monomer and the suspended antimicrobial agent 32 condense on the mask, and not on the masked portions. Portions of the deposition chamber 16 and instrumentation (not shown) for the deposition chamber 16 may be heated to prevent condensation of the parylene monomer and the antimicrobial agent 32 on those portions/instruments.

Figure 2A:
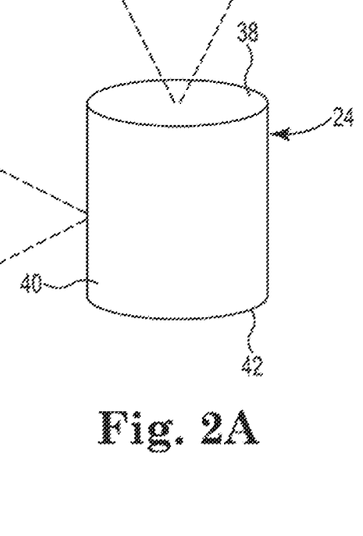
FIG. 2A is a perspective view.
Figure 2B:
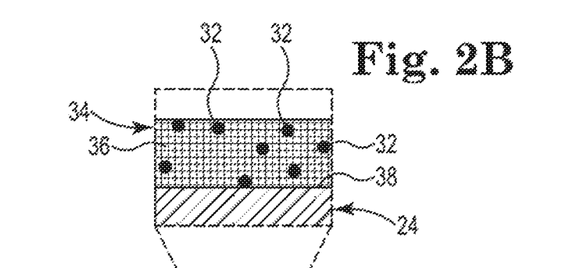
FIGS. 2B and 2C are enlarged schematic cross-sectional views of portions of the surface of the device in FIG. 2A.
Figure 2C:
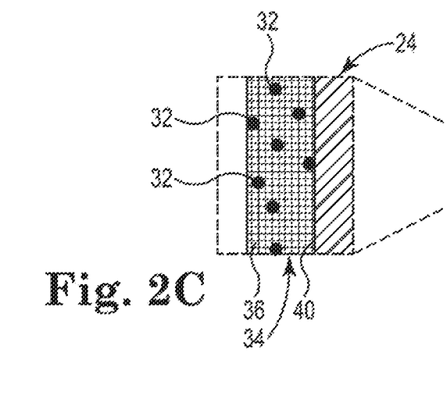

FIGS. 2A, 2B, and 2C are views of the device 24 including the antimicrobial coating 34 on the surface in accordance with embodiments of the present invention. FIG. 2A is a perspective view of the device 24. FIGS. 2B and 2C are enlarged schematic cross-sectional views of portions of the surface of the device 24. In FIG. 2A, the device 24 is shown is after deposition of the antimicrobial coating 34 described above in reference to FIG. 1. As shown in FIG. 2A, the device 24 may be cylindrical in shape and may have a surface including a first surface 38, a second surface 40, and a third surface 42. The first surface 38 may be a flat surface at one end of the device 24, the third surface 42 may be another flat surface at an axially opposite end of the device 24, and the second surface 40 may be a cylindrical surface connecting the first surface 38 to the third surface 42. The second surface 40 may not be parallel to the first surface 38.

In some embodiments, the third surface 42 may be a surface of the device 24 upon which the device 24 rests within the deposition chamber 16 during deposition of the antimicrobial coating 34, and may not be an exposed surface upon which the parylene monomer and the antimicrobial agent 32 condense. Thus, in some embodiments little, if any, antimicrobial coating forms on the third surface 42.

FIG. 2B shows a schematic cross-section of a portion of the first surface 38 covered by the antimicrobial coating 34. As shown in FIG. 2B, the antimicrobial coating 34 includes the parylene polymer 36 and the antimicrobial agent 32. The antimicrobial agent 32 may be a plurality of inorganic antimicrobial particles as described above in reference to FIG. 1. The parylene polymer 36 and the antimicrobial agent 32 may be distributed throughout the antimicrobial coating 34 on the first surface 38.

FIG. 2C shows a schematic cross-section of a portion of the second surface 40 covered by the antimicrobial coating 34. As shown in FIG. 2C, the antimicrobial coating 34 includes the parylene polymer 36 and the antimicrobial agent 32. The antimicrobial agent 32 may be a plurality of inorganic antimicrobial particles as described above in reference to FIG. 1. The parylene polymer 36 and the antimicrobial agent 32 may be distributed throughout the antimicrobial coating 34 on the second surface 40.

In some embodiments, the antimicrobial agent 32 may be present in the antimicrobial coating 34 in an amount as little as about 0.0001 wt. %, about 0.0005 wt. %, about 0.001 wt. %, about 0.005 wt. %, or about 0.01 wt. %, or as great as about 0.1 wt. %, about 0.5 wt. %, about 1 wt. %, about 5 wt. %, or about 10 wt. %, or may be present within any range defined between any pair of the foregoing values. In exemplary embodiments, the antimicrobial agent 32 may be present in the antimicrobial coating 34 in an amount from about 0.0001 wt. % to about 10 wt. %, from about 0.0005 wt. % to about 5 wt. %, from about 0.001 wt. % to about 1 wt. %, from about 0.005 wt. % to about 0.5 wt. %, or from about 0.01 wt. % to about 0.1 wt. %. In some exemplary embodiments, the antimicrobial agent 32 may be present in the antimicrobial coating 34 in an amount of about 0.05 wt. %.

In contrast to some deposition processes, for example, sputter deposition, or e-beam evaporation in which the deposition may be directional, the deposition process for the antimicrobial coating 34 described above in reference to FIG. 1 is a non-directional gas phase deposition process. In this deposition process, the antimicrobial coating 34 may deposit substantially evenly on all exposed surfaces, regardless of the relative orientation of the surfaces. That is, the concentration of the antimicrobial agent 32 in the antimicrobial coating 34 may be substantially the same between the first surface 38 and the second surface 40, even though the surfaces may have different relative orientations because the second surface 40 may not be parallel to the first surface 38. In some embodiments, the concentration of the antimicrobial agent 32 in the antimicrobial coating 34 may not differ between the portion of the first surface 38 and the portion of the second surface 40 by more than as little as about 0.1%, about 0.2%, or about 0.5%, or as much as about 2%, about 5%, or about 10%, or may not differ by more than any amount within any range defined between any pair of the foregoing values. In exemplary embodiments, the concentration of the antimicrobial agent 32 in the antimicrobial coating 34 may not differ between the portion of the first surface 38 and the portion of the second surface 40 by more than from about 0.1% to about 10%, from about 0.2% to about 5%, or from about 0.5% to about 2%. In exemplary embodiments, the concentration of the antimicrobial agent 32 in the antimicrobial coating 34 may not differ between the portion of the first surface 38 and the portion of the second surface 40 by more than about 1%. For example, if the concentration of the antimicrobial agent 32 in the antimicrobial coating 34 on the first surface 38 as shown in FIG. 2B is about 1 wt. %, then the concentration of the antimicrobial agent 32 in the antimicrobial coating 34 on the second surface 40 as shown in FIG. 2C may be within about 1% of the 1 wt. %, or from 0.99 wt. % to 1.01 wt. %.

In some embodiments, the antimicrobial agent 32 may include a plurality of antimicrobial nanoparticles as describe above in reference to FIG. 1, and a plurality of agglomerations of the antimicrobial nanoparticles. In some embodiments, the agglomerations may be as much as about 10,000 times larger than the individual nanoparticles. For example, embodiments employing inorganic antimicrobial nanoparticles having an average diameter of about 100 nanometers may form agglomerations of the antimicrobial nanoparticles as large as 1 millimeter in diameter. In another example, embodiments employing inorganic antimicrobial nanoparticles having an average diameter of about 40 nanometers may form agglomerations of the antimicrobial nanoparticles as large as 0.4 millimeters in diameter.

In some embodiments, after the antimicrobial coating 34 is formed as described above, the antimicrobial coating 34 may be treated with an oxygen containing plasma. It has been found that treating the antimicrobial coating 34 with the oxygen-containing plasma can expose more of the antimicrobial agent 32. Exposing more of the antimicrobial agent 32 may increase the antimicrobial efficacy of the antimicrobial coating 34. In some embodiments, the oxygen-containing plasma is an isotropic plasma, treating the antimicrobial coating 34 across all exposed surfaces.

Embodiments described above provide an antimicrobial coating on medical devices to prevent a transfer of infectious microorganisms from medical devices to a patient. By mixing the antimicrobial agent with the parylene before loading the deposition system, embodiments may employ a commercially available deposition system requiring few, if any, modifications to support the process. Because the antimicrobial coating may be of uniform composition across all exposed surfaces, a desired level of antimicrobial efficacy may be achieved across all exposed surfaces to help prevent nosocomial infections.

EXAMPLES

The present invention is more particularly described in the following examples that are intended as illustrations only, since numerous modifications and variations within the scope of the present invention will be apparent to those of skill in the art. Unless otherwise noted, all parts, percentages, and ratios reported in the following examples are on a weight bases, and all reagents used in the examples were obtained, or are available, from the chemical suppliers described below, or may be synthesized by conventional techniques.

Example 1

Deposition of Parylene C and 100 Nanometer Silver Nanoparticles

A mixture was prepared from 100 nanometer diameter silver nanoparticles in dispersion (Sigma-Aldrich, 0.02 mg/mL in aqueous buffer containing sodium citrate as a stabilizer, #730777) and parylene C dimer powder (Specialty Coating Systems, Inc., SCS DPX-C). Approximately 0.10 to 0.15 milliliters (2 to 3 drops) of the silver nanoparticle dispersion was manually mixed with 1.5 grams of the parylene C dimer powder.

The mixture was placed in a removable boat and placed within a vacuum chamber to drive off any liquid. The mixture was then placed within a vaporizer of a parylene deposition system. Air was evacuated from the deposition system, including the vaporizer, and the mixture was heated to 150° C. in the vaporizer to sublimate the dimer and the silver nanoparticles. Then the sublimated dimer was heated to 685° C. to pyrolize the dimer before the pyrolized dimer (monomer) and the silver nanoparticles were deposited on a substrate surface at room temperature to form an antimicrobial coating on the substrate.

Figure 3:
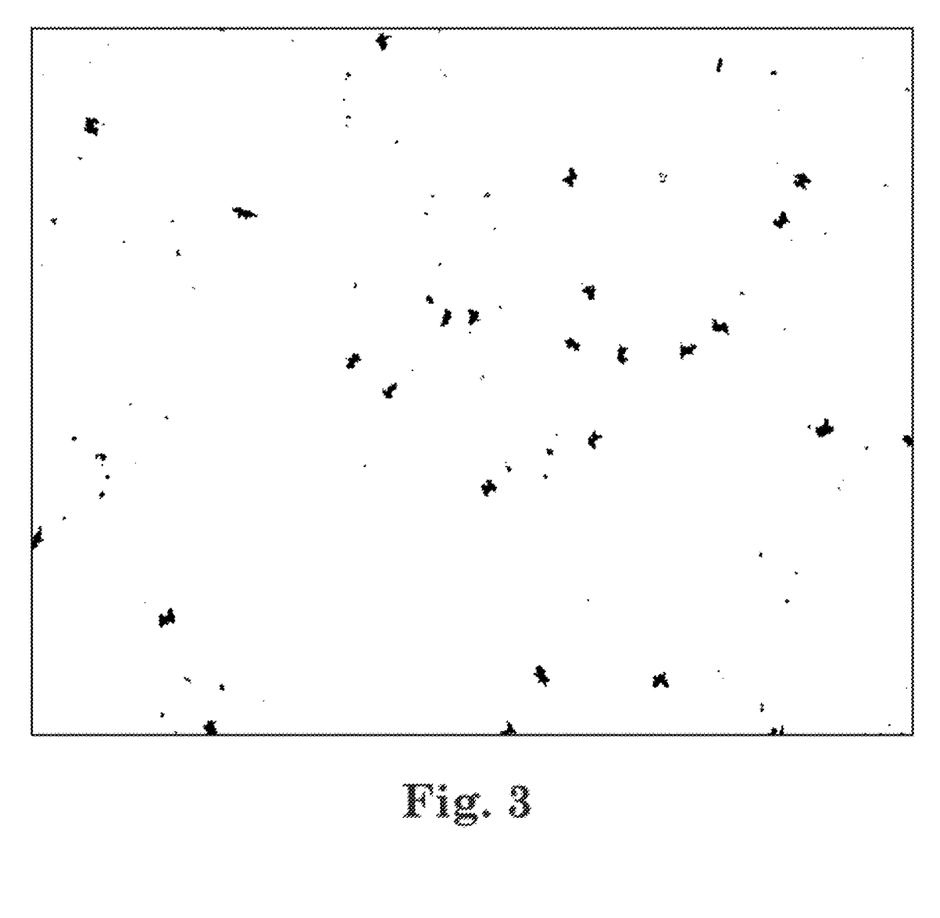
FIG. 3 is a micrograph of an antimicrobial coating on a surface in accordance with embodiments of the present invention.

FIG. 3 is a micrograph of the deposited antimicrobial coating. The micrograph was taken at a magnification of 10 times under a combination of white and ultraviolet lights. As shown in FIG. 3, some of the 100 nanometer nanoparticles have agglomerated to form particles as large as about 1 millimeter in diameter. Agglomerations smaller than about 0.02 millimeters, and any individual 100 nanometer nanoparticles, are not visible in the micrograph. As also shown in FIG. 3, the inorganic antimicrobial particles are integrated into the parylene polymer and distributed throughout the coating.

Example 2

Deposition of Parylene C and 40 Nanometer Silver Nanoparticles

A mixture was prepared from 40 nanometer diameter silver nanoparticles in dispersion (Sigma-Aldrich, 0.02 mg/mL in aqueous buffer containing sodium citrate as a stabilizer, #730807) and parylene C dimer powder (Specialty Coating Systems, Inc., SCS DPX-C). Approximately 0.10 to 0.15 milliliters (2 to 3 drops) of the silver nanoparticle dispersion was manually mixed with 1.5 grams of the parylene C dimer powder.

The mixture was placed in a removable boat and placed within a vacuum chamber to drive off any liquid. The mixture was then placed within a vaporizer of a parylene deposition system. Air was evacuated from the deposition system, including the vaporizer, and the mixture was heated to 150° C. in the vaporizer to sublimate the dimer and the silver nanoparticles. Then the sublimated dimer was heated to 685° C. to pyrolize the dimer before the pyrolized dimer (monomer) and the silver nanoparticles were deposited on a substrate surface at room temperature to form an antimicrobial coating on the substrate.

The antimicrobial coating was viewed at a magnification of 50 times under ultraviolet light. Some of the 40 nanometer nanoparticles had agglomerated to form particles as large as about 0.1 millimeter in diameter. The agglomerations were integrated into the parylene polymer and appeared to be distributed throughout the coating.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for producing an antimicrobial coating on a surface including a first surface and a second surface that is not parallel to the first surface, the method comprising:
    mixing a parylene dimer and an antimicrobial agent to form a mixture;
    heating the mixture under at least a partial vacuum to sublimate the parylene dimer and suspend the antimicrobial agent within the sublimated parylene dimer;
    pyrolyzing the sublimated parylene dimer under at least a partial vacuum to form a parylene monomer, the antimicrobial agent suspended within the parylene monomer; and
    condensing the parylene monomer and the antimicrobial agent together under at least a partial vacuum on the surface to polymerize the parylene monomer and form a coating containing a parylene polymer and the antimicrobial agent, wherein a concentration of the antimicrobial agent in the coating does not differ by more than about 1% between a portion of the first surface and a portion of the second surface.

2. The method of claim 1, further including treating the coating with an oxygen-containing plasma.

3. The method of claim 1, wherein the parylene dimer is selected from the group consisting of [2,2]-paracyclophane, dichloro[2,2]-paracyclophane, tetrachloro-[2,2]-paracyclophane, and octafluoro-[2,2]-paracyclophane.

4. The method of claim 1, wherein the antimicrobial agent is present in the mixture in an amount from about 0.0001 wt. % to about 10 wt. %.

5. The method of claim 1, wherein mixing the parylene dimer and the antimicrobial agent includes mixing the parylene dimer and a plurality of antimicrobial nanoparticles, the antimicrobial nanoparticles having an average diameter less than or equal to about 100 nanometers.

6. The method of claim 5, wherein the antimicrobial nanoparticles have an average diameter greater than or equal to about 20 nanometers and less than or equal to about 60 nanometers.

7. The method of claim 5, wherein the antimicrobial nanoparticles include at least one of metallic gold, metallic silver, metallic copper, and combinations thereof.

8. The method of claim 7, wherein the antimicrobial nanoparticles consist of metallic silver.

9. The method of claim 5, wherein the antimicrobial nanoparticles include at least one of gold salt, a silver salt, a copper salt, and combinations thereof.

10. The method of claim 9, wherein the antimicrobial nanoparticles are selected from a group consisting of silver nitrate, silver chloride, and combinations thereof.

* * * * *